United States Patent [19]

Leslie et al.

[11] Patent Number: 5,187,234

[45] Date of Patent: Feb. 16, 1993

[54] VINYL POLYMERS EXHIBITING NONLINEAR OPTICAL RESPONSE

[75] Inventors: Thomas M. Leslie, Hunstville, Ala.; Ching F. Shu, New Providence, N.J.; Karsten Blatter, Frankfurt, Fed. Rep. of Germany; Ronald DeMartino, Wayne; Frank Battito, West Orange, both of N.J.

[73] Assignee: Hoechst Celanese Corp., Somerville, N.J.

[21] Appl. No.: 755,954

[22] Filed: Sep. 6, 1991

Related U.S. Application Data

[63] Continuation-in-part of Ser. No. 603,982, Oct. 23, 1990, abandoned, and a continuation-in-part of Ser. No. 710,726, Jun. 4, 1991, abandoned.

[51] Int. Cl.$^5$ .......................................... C08F 226/06
[52] U.S. Cl. .................... 525/276; 526/298; 526/311; 526/243; 526/245; 526/259; 526/289; 526/242; 526/248; 526/299; 526/300; 525/279; 525/289; 525/291; 525/292; 525/293; 525/295; 525/297
[58] Field of Search .............. 526/298, 299, 300, 311, 526/242, 243, 245, 248, 259, 279; 525/276, 293, 295, 297

[56] References Cited

FOREIGN PATENT DOCUMENTS 0363232 4/1990 European Pat. Off. .

*Primary Examiner*—Joseph L. Schofer
*Assistant Examiner*—M. Nagumo
*Attorney, Agent, or Firm*—P. S. Kalyanaraman

[57] ABSTRACT

This invention provides novel vinyl polymers with pendant side chains which exhibit nonlinear optical response. The polymers have utility as a transparent optical media in optical devices.

An invention vinyl polymer is illustrated by the acrylate copolymer of the following structure:

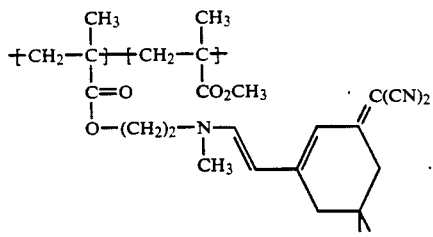

18 Claims, 1 Drawing Sheet

VINYL POLYMERS EXHIBITING NONLINEAR OPTICAL RESPONSE

This application is a continuation-in-part of pending application with Ser. No. 603,982, filed Oct. 23, 1990, now abandoned and of pending application with Ser. No. 710,726, filed Jun. 4, 1991 now abandoned.

BACKGROUND OF THE INVENTION

This invention relates to vinyl polymers that contain, as pendant units, organic moieties that possess high nonlinear optical activity.

Nonlinear optical activities generally result from interaction of materials with light, and are described in terms of second order nonlinearity, third order nonlinearity, and so on. An introduction to the theory and practical applications of nonlinearity, especially of organic materials, is provided by *Nonlinear Optical Properties of Organic Molecules and Crystals*, Volumes. 1 and 2, edited by D. S. Chemla and J. Zyss, Academic Press, 1987.

It is known that organic small molecules and polymeric materials with large delocalized $\pi$-electron systems can exhibit nonlinear optical response, which in many cases is a much larger response than that exhibited by inorganic materials. Examples of such organic small molecules include 2-methyl-4-nitroaniline. Examples of such polymers are described in *Nonlinear Optical Properties of Organic and Polymeric Materials*, ed. D. J. Williams, ACS Symposium Series No. 233, American Chemical Society, Washington, D.C., 1983. Such materials generally contain in their nonlinear molecular units electron donor groups and acceptor groups linked by a conjugated $\pi$-electron unit. This structural pattern gives rise to delocalization of the $\pi$-electrons. The delocalized $\pi$-electrons are believed to give rise to nonlinear effects when the material interacts with high intensity laser radiation. These effects are manifested as generation of different orders of light frequencies called harmonic frequencies.

While a nonlinear molecule can theoretically generate different orders of harmonic frequencies when it interacts with light, it is generally believed that in order to generate the even numbered harmonic frequencies such as second order, fourth order, and the like, the molecule must possess a "non-centrosymmetric" structure. The non-centrosymmetric structure may be inherent in the molecule or induced externally. A theoretical explanation of non-centrosymmetry and its relationship to harmonic generation can be found in *Nonlinear Optical Properties of Organic and Polymeric Materials*, referred to above.

In addition to the possibility of electronic interactions with light, organic and polymeric materials can be modified structurally to suitably optimize properties such as mechanical stability, thermooxidative stability, and laser damage threshold. Laser damage threshold is an expression of the ability of a material to withstand high intensity laser radiation. The utility of a nonlinear optical material frequently is in a device where the material is subjected to high intensity laser radiation. Unless the material is capable of withstanding such radiation, the device may fail in its intended function.

Furthermore, several organic polymers can be cast as thin films by techniques well known in the art. Thin films have the advantage of better utility than single crystals in device fabrication. Inorganic materials generally are single crystals.

Thin films of organic or polymeric materials with large second order nonlinearities in combination with silicon-based electronic circuitry have potential utilities in devices for laser modulation and deflection, information control in optical circuitry and the like. Novel processes occurring through third order nonlinearity such as degenerate four-wave mixing, whereby real-time processing of optical fields occurs, have potential utility in devices that have applications in such diverse fields as optical communications and integrated circuitry. Devices based on optical nonlinearity of materials are described in, for example, U.S. Pat. Nos. 3,234,475; 3,395,329; 3,694,055; 4,428,873; 4,515,429; 4,583,818; and by P. W. Smith et al in *Applied Physics Letters*, 30(6),280 (1977). Devices based on organic materials with conjugated electron systems are described, for example, in U.S. Pat. No. 4,865,406.

Nonlinear optical materials can be used either as small molecules in a guest-host combination or, more preferably, as a covalently linked part of organic polymers. Guest-host combinations are physical mixtures of a nonlinear small molecule and a film-forming polymer. Such mixtures have a number of disadvantages including insufficient loading of the nonlinear material, and possible phase separations. In contrast to the guest-host combination, polymer systems where the nonlinear optical moiety is covalently linked to the polymer chain avoid such disadvantages, and are generally referred to as nonlinear optical polymers.

Even though the individual nonlinear optical moieties in a polymer may possess inherently high activity, the overall activity in the polymer may be enhanced or reduced by orientation of the dipoles in the individual moieties. Thus, if the dipoles are oriented parallel to each other, the overall activity may be enhanced. If the dipoles are oriented opposite to each other, the overall activity may be substantially reduced or even zero. In order to enhance the overall activity of a polymer, the dipoles are typically oriented after the polymer is cast as a film. Several techniques, electrical, magnetic as well as mechanical, are available for such orientation, and are described in U.S. Pat. No. 4,913,844.

A well known and frequently used technique is "poling". During poling, the film is generally heated to a higher than ambient temperature, typically near the glass transition temperature ($T_g$), and oriented in an applied electrical field; this orientation is then "frozen" in the polymer during a typical cooling process. Usually, better orientation is achieved by using higher electrical fields. However, the capacity to withstand high electrical field strengths differs among polymer films. Nonlinear optical polymers that can withstand high electric fields are preferred by those skilled in the art due to the possibility of achieving higher orientation of the dipoles.

Nonlinear moieties can be covalently linked to a polymer in either of two ways. They may exist as part of the main chain of the polymer or as pendant side groups. For example, EP 89402476.9 discloses main chain polymers such as polyurethanes or polyesters formed from difunctional nonlinear optical materials. A typical example disclosed has recurring units shown in Formula I:

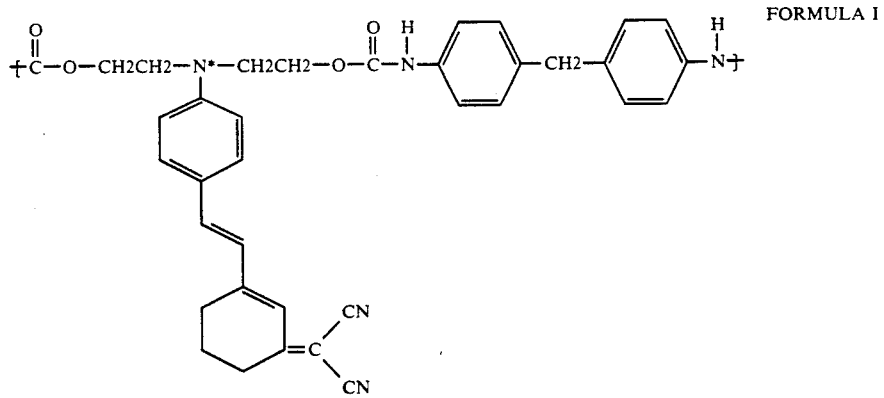

FORMULA I

In Formula I, the nonlinear optical moiety (indicated by the grouping starting from N. and terminating at the two cyano groups) contains the nitrogen of the amine functionality as the electron donor, and the cyano groups as the electron acceptor, linked via a conjugated electron system. The electron donor nitrogen is part of the main chain polymer backbone.

Examples of polymers that contain nonlinear optical moieties as pendant side groups are described in U.S. Pat. Nos. 4,779,961; 4,801,670; 4,808,332; 4,865,430 and 4,913,844. The polymers disclosed by, for example, U.S. Pat. No. 4,865,430 include materials of Formula II:

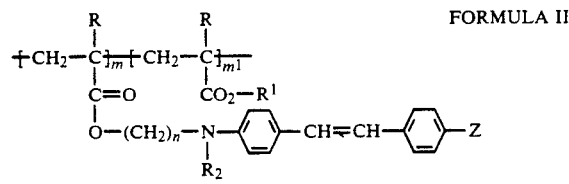

FORMULA II where m and $m^1$ are integers which total at least 10, and the m monomer comprises between about 10-90 mole percent of the total $m+m^1$ monomer units; R is hydrogen or a C1–C4 alkyl, C6–C10 aryl, halo or haloalkyl substituent; n is an integer between 1 and about 12; $R^1$ is a C1–C6 alkyl substituent; $R_2$ is hydrogen or a C1–C4 alkyl substituent; and Z is a nitro or cyano substituent. The material of Example I in the same patent is shown in Formula III:

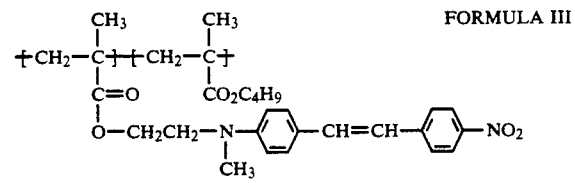

FORMULA III

In Formula III, the nitrogen donor atom and the nitro acceptor group are linked via a stilbene unit, and the nonlinear optical moiety is attached to the polymer backbone as a side chain. This material of Formula III is a copolymer, formed from two comonomers. In the case of copolymers, the comonomer or comonomers chosen may also carry nonlinear optical side chains. Additionally, comonomers can be suitably chosen to enhance the quality and transparency of the films obtained from the copolymer. The choice of a wide variety of comonomers available renders fine tuning of polymer properties readily achievable.

While such polymers exhibit good nonlinear optical activity, increasing sophistication of devices demands higher levels of such activity in polymers. Thus, there is a continuing interest in the preparation of novel polymers and copolymers containing nonlinear optical moieties with high activity. There is also an increased effort to develop novel nonlinear optical devices based on such polymers.

Accordingly, it is an object of this invention to provide novel vinyl polymers with pendant side chains which exhibit high nonlinear optical response.

It is yet another object of this invention to provide novel side chain vinyl polymers which can be poled at high field strengths.

It is a further object of this invention to provide nonlinear optical media incorporating a transparent nonlinear optical component which comprises such vinyl polymers.

Other objects and advantages of the present invention shall become apparent from the accompanying description and examples.

SUMMARY OF THE INVENTION

The present invention is directed to a vinyl polymer which has nonlinear optical moieties in its side chains, and is characterized by recurring monomeric units represented in Formula IVa:

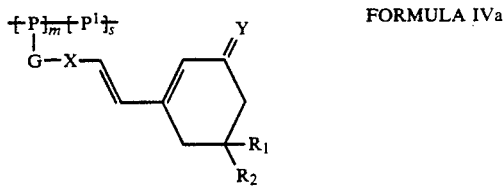

FORMULA IVa where P and $P^1$ represent vinyl monomer moieties forming the polymer backbone, m and s are integers which total at least 10, and the m monomer comprises between about 10-100 mole percent of the total (m+s) monomer units; G represents a spacer group, $R_1$ and $R_2$ may be the same or different and are selected from the group consisting of hydrogen, C1–C6 alkyls and C1–C6 haloalkyls; X represents an electron donor group capable of donating electrons to the pi-system, and Y represents an electron acceptor group.

When the spacer group G is one or more methylene groups, the polymer can be represented by the recurring units shown in Formula IVb:

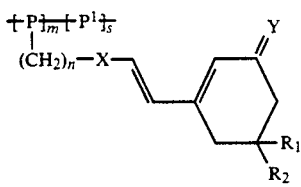

FORMULA IVb where P, $P^1$, m, s, $R_1$, $R_2$, X and Y are the same as described above, and n is an integer between 1 and about 12. Some typical examples of X include

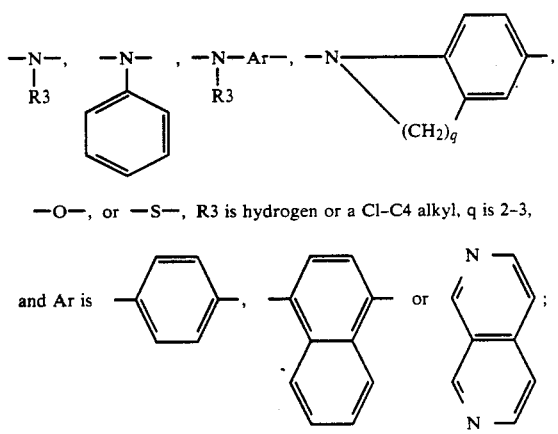

—O—, or —S—, R3 is hydrogen or a Cl-C4 alkyl, q is 2-3,

Some typical examples of Y include $C(CN)_2$, C(H)(CN), $C(H)(NO_2)$, $C(H)(CF_3)$, $C(H)(SO_2CH_3)$, or $C(H)(SO_2CF_3)$. When s is zero, the polymer is a homopolymer of the vinyl monomer containing the nonlinear optical unit in the side chain. When m is less than 100 mole percent of the total (m+s) monomer units, the composition is a copolymer of the two vinyl monomers. Formula IV depicts the nonlinear optical moiety attached to only the m monomer; however, the s monomer may also independently carry a nonlinear optical moiety in its side chain. Furthermore, while Formula IV shows only one double bond between X and the cyclohexene ring, it is conceivable to have more than one double bond there existing in conjugation with the other double bonds. For example, an additional double bond in that position would make it a butadiene unit between X and the cyclohexene ring.

The present invention also relates to formation of solid film media having an induced non-centrosymmetric structure using the vinyl polymers of the invention. The polymers of this invention have very good solubility in common organic solvents such as halogenated hydrocarbons, ketones, esters, and the like, and can be cast as films, using methods known to those skilled in the art, to obtain films with excellent transparency. The term "transparent" as employed herein refers to an optical medium which is transparent or light transmitting with respect to entering light frequencies (called fundamental frequencies) as well as created light frequencies (called harmonic frequencies) which is explained below.

When light of suitable fundamental frequency enters a nonlinear optical medium, the medium can generate different orders of harmonic frequencies of that fundamental frequency, and these are in turn referred to as second harmonic, third harmonic, and so on. An ideal medium should be transparent to all these frequencies without significant scattering of light. The medium of the present invention is transparent to both fundamental and harmonic frequencies with less than 15 percent scattering.

The nonlinearity of the different orders of harmonics are measured and expressed in terms of a quantity called susceptibility. Thus, the second harmonic is expressed by a quantity called second order susceptibility, denoted $\chi 2$, the third harmonic is expressed by a quantity called third order susceptibility, denoted $\chi 3$, and so on. Yet another frequently measured and expressed property is the linear electrooptic coefficient, r. Measurement of quantities such as $\chi 2$, $\chi 3$, and r are well known in the literature, and are typically used to characterize and evaluate the nonlinearity of materials. A detailed explanation of the above terms and their measurement techniques can be found in *Nonlinear Optical Properties of Organic Molecules and Crystals*, Volumes 1 and 2, mentioned earlier. Furthermore, C. C. Teng et al (*Applied Physics Letters*, Vol. 56, 1734 1990)), incorporated herein by reference, describe a simple reflection technique for measuring the r value of poled polymers.

The higher the nonlinearity of a medium is, the greater are the values for $\chi 2$, $\chi 3$, and r, and the greater is the utility of the medium for fabricating nonlinear optical devices. It is believed that side chain organic polymers are preferable for such devices because of the unique possibility to append a great number of nonlinear optical moieties on the polymer backbone, and because of the possibility of enhancement of the activity of such moieties during orientation by field-induced poling. The polymer of the present invention shows much higher values for $\chi 2$, $\chi 3$ and r and withstands higher field strengths than the main chain polymers disclosed by, for example, EP 89402476.9 listed above.

Due to its excellent film characteristics, harmonic generation, and very low light scattering, the film made from the polymer of the invention is ideally suited for fabricating nonlinear optical devices, such as frequency doublers, optical switches, light modulators, and the like. Other typical nonlinear optical devices are described in U.S. Pat. No. 4,865,406, mentioned earlier.

BRIEF SUMMARY OF THE DRAWING

The invention is described in detail below with reference to the single FIGURE (FIG. 1) which is a plot of electrooptic coefficient versus poling field.

DETAILED DESCRIPTION OF THE INVENTION

Figure 1:
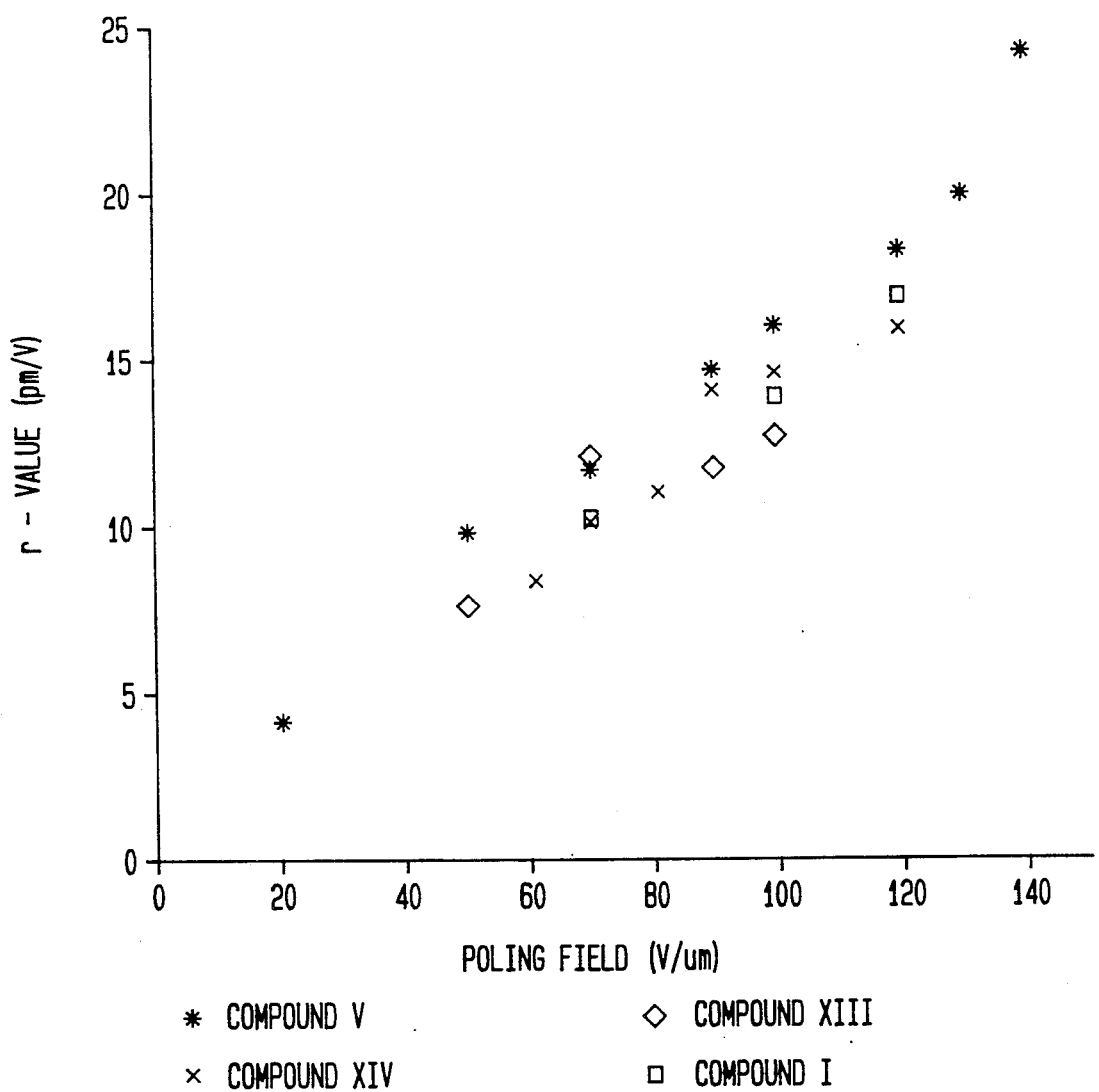

The present invention relates to vinyl polymers that carry nonlinear optical moieties as pendant units. Vinyl polymers, in general, are obtained by polymerization of vinyl monomers, and are described in *Textbook of Polymer Science*, by F. W. Billmeyer, Jr., 3rd edition, John Wiley & Sons, 1984, page 49. Some typical vinyl monomers include acrylates, styrenic monomers, vinyl acetate, vinyl chloride, vinyl cyanide, maleic anhydride, maleimide, and the like. The present invention is described here as an acrylate copolymer of Formula V:

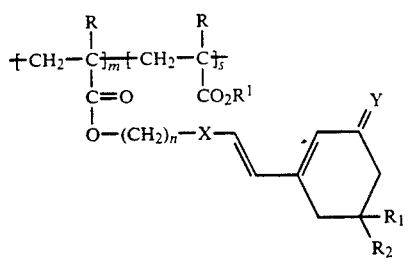

FORMULA V where m and s are equal in molar quantities, R, $R_1$, $R_2$, and $R^1$ are methyl groups, n equals 2, X is

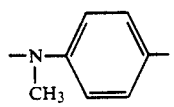

and Y is $=C(CN)_2$.

However, it will be understood that such description is exemplary only and is for purposes of exposition and not for purposes of limitation.

The desired copolymer is made, as outlined in Scheme I, by copolymerizing two methacrylate monomers, one monomer carrying the nonlinear optical moiety in its ester part as illustrated in formula VI, and the other monomer being methyl methacrylate (XII):

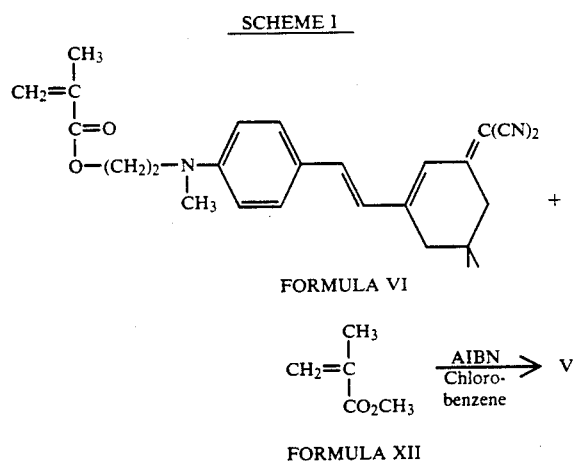

Scheme I describes the copolymerization of VI and XII using a free radical initiator, azobisisobutyronitrile (AIBN), in chlorobenzene. A detailed description of this polymerization reaction is given in the 'Description' section below.

A typical process to synthesize a compound of Formula VI is illustrated in Scheme II:

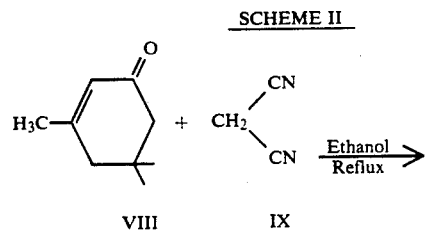

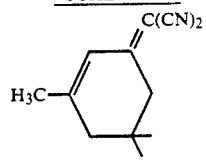

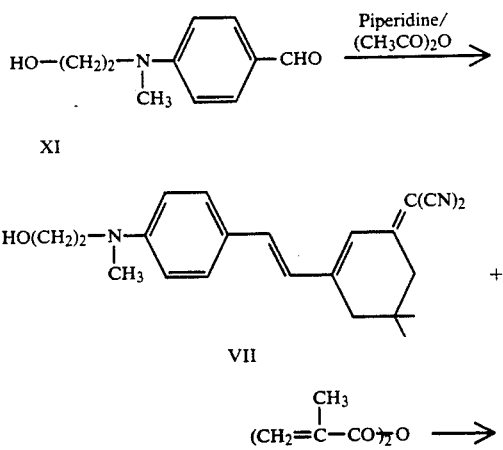

The starting material for the synthesis of a material of Formula VI is a compound of Formula VII, which is prepared following the procedure described by R. Lemke in *Synthesis*, (1974), pages 359-361. Thus, isophorone of Formula VIII and malononitrile of Formula IX are condensed in a suitable solvent such as ethanol to form the intermediate of Formula X. The reaction is done at temperatures preferably above 40° C., and typically at reflux conditions. When ethanol is the solvent, these reflux conditions are about 80° C. The product of Formula X is used directly in the next step of the reaction in the same pot. If desired, product X could be isolated by filtration and purified by recrystallization from a suitable solvent such as toluene.

The product X may be reacted in the same pot with a suitable aldehyde. In this illustration, the aldehyde is 4-[N-(2-hydroxyethyl)-N-methyl]-benzaldehyde of Formula XI. The reaction is done under conditions suitable for effecting a Knoevenagel condensation between the two reactants. Knoevenagel condensations are described by G. Jones in *Organic Reactions*, Vol. 16, John Wiley & Sons, 1967. The reaction is preferably performed at temperatures higher than ambient temperature, typically around the reflux temperature, for a time period of 1-24 hours, typically and conveniently overnight. The product VII can be isolated as a solid and, if necessary, recrystallized from a suitable solvent such as toluene. If it is substantially pure as shown by analytical techniques such as thin layer chromatography, and NMR spectrum, it can be directly used in the next step.

The product VII can be esterified to a compound of Formula VI in a variety of conventional ways, such as, for example, reacting a compound of Formula VII with an acid chloride or an anhydride. In a typical process to make a compound of Formula VI, a compound of Formula VII is reacted with methacrylic anhydride, in a suitable solvent such as ethyl acetate, optionally employing a suitable catalyst, such as, for example, 4-dimethylaminopyridine. Typically, ambient temperature conditions are adequate, with stirring between ½ and 48 hours, typically around 2-8 hours. The progress of the reaction may be followed by thin layer chromatography on a suitable adsorbent such as silica gel, with a suitable solvent such as ethyl acetate. When the reaction is complete, the product may be isolated and purified by methods familiar to those skilled in the art. In the above typical example, the compound of Formula VI is purified by recrystallization from a suitable solvent such as toluene. The purity and confirmation of its structure may be done by typical analytical techniques such as thin layer chromatography, NMR spectrum, and elemental analysis.

Copolymerization of compound VI with compound XII can be done in a variety of suitable ways, such as those described in *Textbook of Polymer Science*, ed. by F. Billmeyer, Jr., 3rd ed., John Wiley & Sons, 1984. Free radical polymerization process is a convenient method. Thus, in a typical reaction to make a 1:1 copolymer of compound VI and compound XII, compound VI and compound XII are taken in a suitable solvent such as chlorobenzene, which is degassed and kept under an inert gas atmosphere such as argon. The reaction mixture is then heated with stirring to temperatures above 40° C., while a solution of a suitable free radical initiator, such as azobisisobutyronitrile (AIBN), in a suitable solvent such as chlorobenzene is added in quantities sufficient to initiate the polymerization and to form a polymer with the desired molecular weight, such as, for example, in the range of 5,000-500,000. It is believed that the reaction temperature and time influence the molecular weight of the product. In a typical reaction, the temperature is maintained at around 60°-65° C. for a period of about 48 hours. The reaction is then cooled and the product is isolated by pouring it into a nonsolvent, such as methanol, and filtered. If necessary, the product may be purified by dissolving it in a solvent such as tetrahydrofuran and reprecipitating it from methanol. The filtered and dried copolymer can be analyzed by customary techniques well known to those skilled in the art, such as, for example, NMR spectrometry, elemental analysis, gel permeation chromatography, high pressure liquid chromatography, thermal analysis, and the like.

While the above description teaches the preparation of the monomer VI from compound of formula VII and subsequent polymerization of the monomer, compound VII may be directly linked to a pre-formed polymer or copolymer too. For example, a pre-formed or commercially available maleic anhydride-styrene copolymer (Formula XV) of suitable molecular weight can be reacted with compound of formula VII to form copolymer XVI as shown in Scheme III:

SCHEME III

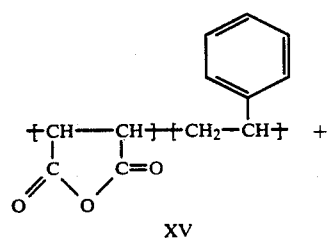

XV

-continued
SCHEME III

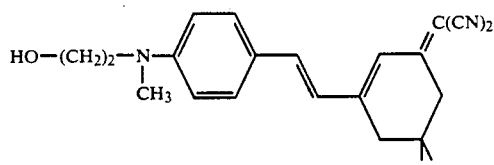

VII

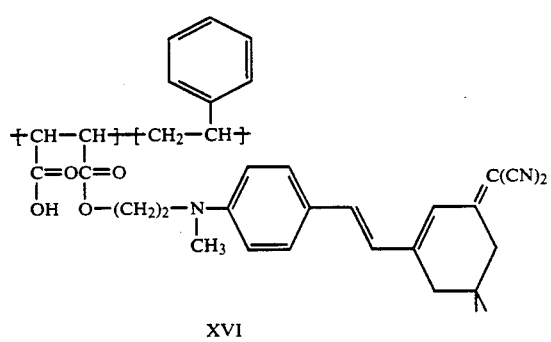

XVI

The foregoing polymers may be used to form films by any suitable technique known to those skilled in the art, such as spin coating, dip coating, brush coating, and the like. Generally spin coating is preferred due to its simplicity and speed. For a typical spin coating experiment, a solution of polymer V is made in a suitable concentration using a suitable solvent such as cyclohexanone. The solution is typically filtered through microporous membranes made of polytetrafluoroethylene (Teflon ®, from E. I. duPont de Nemours & Co., Wilmington, Delaware) to remove any insolubles. The filtered solution can be spin coated onto suitable substrates such as, for example, glass, silicon wafers, aluminum wafers, and the like. In a typical example, the solution is spin coated onto glass slides that had previously been coated with a conducting material, such as indium-tin-oxide (ITO), at spin speeds ranging from 200-5,000 revolutions per minute (rpm), for periods ranging from about 20-200 seconds. Drying of the coatings leaves good films with high transparency.

Poling of a film from polymer of Formula V under applied electric fields, and measurement of the electrooptic coefficient, r, under poled conditions may be done following the procedure of C. C. Teng et al, *Applied Physics Letters*, Vol. 56, 1734 (1990), cited above. In a typical poling experiment, the polymer film is coated with a conducting material such as gold. This gold layer and the ITO coating serve as opposite electrodes in the experiment. The polymer sample is heated to a temperature within a range of about $T_g \pm 5°$ C. and an electric poling field is applied across the electrodes for a period of about 4-7 minutes. The sample is then slowly cooled back to near ambient temperature when power is turned off.

For measuring the electrooptic coefficient r, a collimated laser beam of wavelength 1.304 μm is allowed to enter the sample through the glass substrate, the ITO coating, polymer film, and reflect off the gold substrate. A field of about 50 volts is applied across the sample as a modulating field. The output beam goes to a detector, and is measured against the reference signal. The value of r is determined by varying the phase of the incident laser light and measuring the maximum and minimum DC intensities directly form the detector, and analyzing the data following the procedure of C. C. Teng et al, above. The measurements are performed after poling the film at several electric field strengths, ranging from 20 to 140 Volts per micrometers (V/μm).

The values of r obtained from a typical measurement on films of Formula V are compared against r values of films of the main chain polymers represented by the recurring units shown in Formulas XIII, XIV, and I:

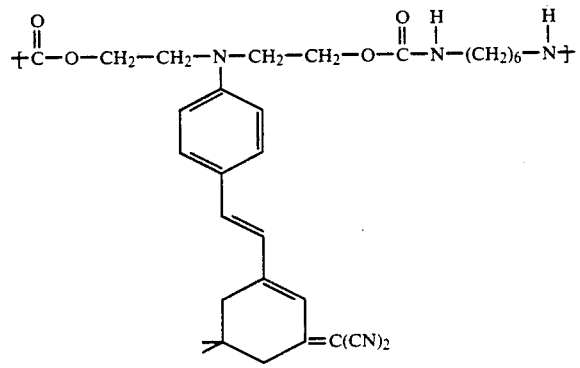

FORMULA XIII

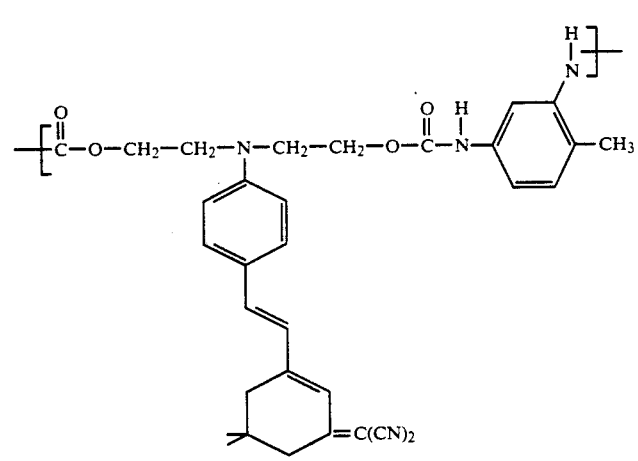

FORMULA XIV

Polymers of Formulas XIII, XIV and I contain the same nonlinear optical moiety as polymer of Formula V; however, in Formulas XIII, XIV and I, the nitrogen donor atom of the nonlinear optical moiety forms a part of the main chain, whereas, in Formula V, the entire nonlinear optical moiety is present as a side chain appended to a polymer backbone. The results, shown in FIG. 1, demonstrate that films made from polymer of Formula V surprisingly show consistently higher value for r than the polymers of Formulas XIII, XIV and I, at virtually all the poling field strengths. This indicates the superiority of poling-induced orientation of nonlinear optical moieties achievable with the side chain polymers of the present invention. In addition, the films from polymers of Formulas XIII, XIV, and I broke down at field strengths higher than 120 V/μm, so that measurements at higher than 120 V/μm fields could not be carried out. The film from polymer of Formula V, on the other hand, was stable and maintained its integrity to at least 140 V/μm fields, thereby showing its superiority.

The following nonlimiting examples are provided in order to further illustrate the present invention.

EXAMPLES

In the following Examples, g refers to grams, ml to milliliters, mole refers to millimole, ° C. to degrees Celsius, μm to micrometers, Rf to Retention Factor, and ambient temperature, ranges between 20°–28° C.

EXAMPLE 1: PREPARATION OF A COMPOUND OF FORMULA VII

Ethanol (1200 ml), isophorone (276 grams), and malononitrile (132 grams) were added together in a 3 liter 3 necked round-bottom flask, and stirred with a magnetic stirring bar in the presence of nitrogen at ambient temperature for about ½ hour. The mixture turned a brownish color. Piperidine (30 grams), acetic acid (6 grams), and acetic anhydride (4 grams) were added in that order to the flask, and the mixture was then heated with stirring to reflux. Into the same flask was added 4-[N-(2-hydroxyethyl)-N-methyl]-benzaldehyde (350 grams). The mixture turned deep red. The mixture was stirred for about an additional 4 hours. Heating was then stopped, and the mixture was allowed to cool overnight. The product that had crystallized overnight was analyzed by thin layer chromatography (silica gel with ethyl acetate:hexane (1:1) as eluent; $R_f$ was about 0.35). The product was filtered, washed with a little ethanol, and dried.

EXAMPLE 2: PREPARATION OF A COMPOUND OF FORMULA VI

Ethyl acetate (250 ml) was kept stirring with a stirring bar in the presence of nitrogen at ambient temperature in a 1 liter 3 necked flask, while a mixture of the product from Example 1 (17.35 grams, 0.05 mole), freshly distilled methacrylic anhydride (8.48 grams, 0.055 mole), and 4-dimethylaminopyridine (0.61 gram, 0.005 mole) was added to it. Stirring at ambient temperature was continued for about 5 hours. Examination by thin layer chromatography (silica gel; ethyl acetate as eluent) showed an absence of any starting material. The reaction solution was concentrated to about 50 ml, to which about 200 ml of n-hexane was added to precipitate the product. The product was filtered, and then purified by column chromatography over silica gel using ethyl acetate:hexane (2:1) as eluent, and recrystalized from toluene. Yield: 14.5 grams, m.p. 115°–118° C.

EXAMPLE 3: PREPARATION OF THE COPOLYMER OF FORMULA V

A 250 ml round bottom flask with a stoppered side arm was equipped with a magnetic stirring bar, and water-cooled condenser, with provision to maintain a presence of argon from the top of the condenser. A portion of the product from Example 2 (8.3 grams, 20 mole), freshly distilled methyl methacrylate monomer (2.0 gram, 20 mole), and chlorobenzene (40 ml) were added to the flask. The mixture formed an intense red color. The mixture was degassed about six times under argon atmosphere. The flask was then lowered into an oil bath at ambient temperature. The bath was then heated to 65° C. with stirring under an argon atmosphere. The bath was thermostatically maintained at 65° C. A degassed 2 weight percent solution of azobisisobutyronitrile (AIBN) (1 ml, 0.3 molar % ratio with respect to the monomers) in chlorobenzene was added via syringe. After stirring for 24 hours, the heating was stopped, and the mixture was poured into a blender and blended with about 600 ml of methanol. It was then filtered to isolate the polymer of Formula V. The product was washed with methanol, and dried at ambient temperature.

The product was purified by dissolving it in tetrahydrofuran (200 ml), and reprecipitating it with 700 ml methanol. The product was then filtered, and the purification was repeated once more. The purified product was then filtered, washed with 100 ml methanol, and dried under vacuum at ambient temperature. (yield: 6.44 grams), $T_g$: 147.8° C.; $M_w$: 155,000; $M_n$: 100,000.

EXAMPLE 4: PREPARATION OF FILM MADE FROM A POLYMER OF FORMULA V ON GLASS SUBSTRATES

A portion of the material from Example 3 (2.309 grams) was added to cyclohexanone (13.043 grams) in a 50 ml flask and stirred with a stirring bar at ambient temperature overnight to obtain a 15 weight percent solution. This solution was filtered first through glass fiber, then through a Gelman brand polytetrafluoroethylene (Teflon ®) membrane (1.0 μm size), and finally through a Gelman brand polytetrafluoroethylene (Teflon ®) membrane (0.2 μm pore size) under nitrogen atmosphere.

The solution was spin coated at 1500 rpm for 20 seconds onto two glass slides (1 inch × 2 inches) that had been previously been coated with Indium-Tin-Oxide. The slides were dried under nitrogen atmosphere for about 3 hours at about 122° C., followed by slow cooling to ambient temperature. These slides were used in Examples 5 and 6.

In a similar manner, films were also made from polymers of the Formulas XIII, XIV, and I and used in Examples 5 and 6.

EXAMPLE 5: POLING OF FILM MADE FORM POLYMER OF FORMULA V

A slide from Example 4, containing film of polymer or Formula V, was placed in an Edward's Vacuum Coating System (Model No.: E-306A, from Edward's Temescal, Division of BOC Group,Inc., Berkeley, California). A gold layer of 1500 Angstroms thickness was deposited on the polymer film in a pattern of small circles, each circle about 0.25 inch in diameter. A 38 gauge wire was then attached to a gold electrode circle and to the ITO layer using conductive silver paint Catalog No.: 14810, from Ernest Fullam, Inc., Latham, New York). The sample was then placed on a Mettler Hot Stage (model No.: FP 82HT, from Mettler Instruments Corp., Hightstown, New Jersey) and heated to a temperature in range of about 142°–152° C. A poling DC electrical field (see Table 1 and FIG. 1) of 20 V/μm, was applied across the electrodes for a period of about 5 minutes. The sample was then allowed to cool back to about 30° C. over a duration of about 30 minutes when the field was turned off. The sample was then cooled to ambient conditions. The r value corresponding to this poling field Of 20 μm was measured as described in Example 6 below. The poling field was then changed (at the same gold circle-38 gauge wire-ITO electrode) and r value was measured again at the new field strength. Thus, the same electrode combination could be used without breakdowns for at least 9 measurements. If the electrode combination breaks down, another gold circle was chosen for the rest of the measurements.

In a similar manner, the films made in Example 4 from comparative polymers of Formulas XIII, XIV and I were also poled at the various electrical fields shown in Table 1 and FIG. 1.

EXAMPLE 6: MEASUREMENT OF R VALUE

For this measurement, a collimated laser diode of wavelength 1.304 μm (Model No.: S1102, from Electrooptics Corp., Boulder, Colorado) was used. A poled sample of polymer of Formula V from Example 5 (poled at 20 V/μm ) was held vertically and then rotated to an angle of 45° with respect to the incoming laser beam. The laser beam, polarized at 45°, passed through a Soleil Babinet compensator (Model No.: 8-400-IR, from Special Optics, Little Falls, New Jersey) and was incident upon the sample. The light entered through the glass substrate, passed through the ITO coating and polymer film, and reflected off the gold electrode and out making a 90° turn. The reflected light then passed through an analyzing polarizer to a germanium photodetector (Model No.: 818-IR, from Newport Corp., Fountain Valley, California). A 1000 Hertz AC electrical signal of about 50 volts was applied across the sample as a modulating field. This frequency was also supplied to a lock-in amplifier (Model No.: SR530, from Stanford Research Systems, Sunnyvale, California) as a reference signal. The output of the detector was the input signal to the lock-in amplifier and was referenced to the modulating frequency. The value of r was determined by varying the phase of the incident laser light using the Soleil Babinet compensator and measuring the maximum and minimum DC intensities directly from the detector. The compensator was then adjusted until the detector received the average of these two intensities. At this point the modulated signal could be read directly from the lock-in amplifier. The compensator was then tuned through either a maximum or a minimum to a point where the average DC intensity level was detected. The modulated signal was again read from the lock-in amplifier and the two readings were averaged. Analysis of the data was done using the procedure of C. C. Teng et al, referred to above. The value of r at the poling field strength of 20 μm/V was found to be 4.1.

In a similar manner, r value was measured at poling fields higher than 20 V/μm on samples from polymer of Formula V. The value of r was also measured on poled samples from polymers of Formula XIII, XIV and I. The results are summarized in Table 1 and FIG. 1. Examples 6 through 13 in Table 1 represent r values for polymer of Formula V at poling fields of 20-140 V/μm; examples 14 through 17 give the values of r for polymer of Formula XIII at poling fields of 30-100 V/μm; examples 18 through 23 represent the values of r for polymer of Formula XIV at fields of 60-120 V/μm; and examples 24 through 26 represent r values for polymer of Formula I at fields of 70-120 V/μm. As Table 1 and FIG. 1 show, the values of r surprisingly were higher for polymer of Formula V than those for polymers XIII, XIV and I. Furthermore, only polymer of Formula V could withstand poling fields higher than 120 V/μm; polymers XIII, XIV and I broke down at fields of above 120 V/μm.

TABLE 1 r values at different poling fields for polymers of Formula V, XIII, XIV and I.

| Example No. | Polymer Formula | Poling Field (V/μm) | r |
|---|---|---|---|
| 6 | V | 20 | 4.1 |
| 7 | V | 50 | 9.8 |
| 8 | V | 70 | 11.7 |
| 9 | V | 90 | 14.7 |
| 10 | V | 100 | 16.1 |
| 11 | V | 120 | 18.3 |
| 12 | V | 130 | 20.0 |
| 13 | V | 140 | 24.3 |
| 14 | XIII | 50 | 7.6 |
| 15 | XIII | 70 | 12.1 |
| 16 | XIII | 90 | 11.8 |
| 17 | XIII | 100 | 12.7 |
| 18 | XIV | 60 | 8.5 |
| 19 | XIV | 70 | 10.2 |
| 20 | XIV | 80 | 11.2 |
| 21 | XIV | 90 | 14.3 |
| 22 | XIV | 100 | 14.8 |
| 23 | XIV | 120 | 16.2 |
| 24 | I | 70 | 10.3 |
| 25 | I | 100 | 13.9 |
| 26 | I | 120 | 17 |

EXAMPLE 27: PREPARATION OF POLYMER XVI

A portion of the compound of formula VII from Example 1 (34.7 grams, 0.1 mole) was added to a stirring solution of a 50/50 copolymer of maleic anhydrice/styrene (20.2 grams, 0.1 mole, $M_N$ 1600, available from Polysciences, Inc., Warrington, Pennsylvania) in tetrahydrofuran (150 ml) in a reaction flask. 4-Dimethylaminopyridine (16 grams, 0.13 mole) was added, and the reaction mixture heated under reflux for 3.5 hours. The reaction mixture was then poured into toluene (2500 ml), and the resultant precipitate was recovered by filtration. The solid product was dissolved in a 15% solution of acetic acid in tetrahydrofuran and reprecipitated in toluene. The polymer was then recovered by filtration and dried. The polymer had a $T_g$ of about 110° C.

What is claimed is:

1. A vinyl polymer which is characterized by recurring monomeric units corresponding to the formula:

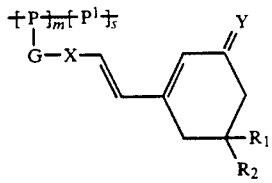

where P and $P^1$ represent vinyl monomer moieties forming the polymer backbone, m and s are integers which total at least 10, and the m monomer comprises between about 10-100 mole percent of the total (m+s) monomer units; G represents a spacer group, $R_1$ and $R_2$ may be the same or different and are selected from the group consisting of hydrogen, C1-C6 alkyls and C1-C6 haloalkyls; X represents an electron donor group that donates electrons to the pi-system, and Y represents an electron acceptor group.

2. The vinyl polymer as described in claim 1, where G is the group —CHR— where R represents hydrogen, a C1-C6 alkyl, or a C1-C6 haloalkyl.

3. The vinyl polymer as described in claim 1, which has a weight average molecular weight between about 5,000-500,000.

4. The vinyl polymer as described in claim 1, which has a glass transition temperature in the range between 40°-220° C.

5. A transparent nonlinear optical medium comprising a polymer in accordance with claim 1.

6. A transparent nonlinear optical medium in accordance with claim 5, which is characterized by an external field-induced orientation of aligned m monomer units.

7. A vinyl polymer which is characterized by recurring monomeric units corresponding to the formula:

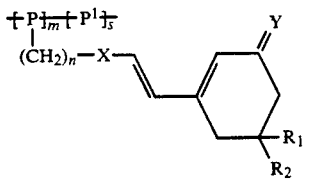

where P and $P^1$ represent vinyl monomer moieties forming the polymer backbgone, m and s are integers which total at least 10, and the m monomer comprises between about 10-100 mole percent of the total (m+s) monomer units; n is an integer between 1 and about 12; $R_1$ and $R_2$ may be the same or different and are selected from the group consisting of hydrogen, C1-C6 alkyls and C1-C6 haloalkyls; X is

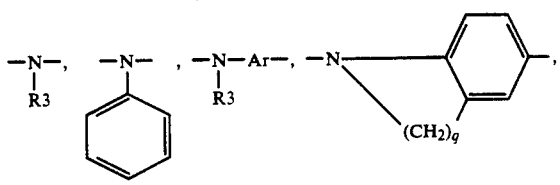

—O—, or —S—, R3 is hydrogen or a C1-C4 alkyl, q is 2-3, and Ar is 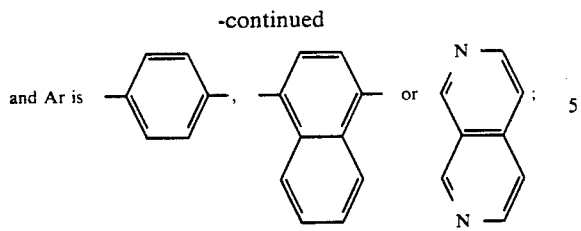

and Y is $C(CN)_2$, $C(H)(CN)$, $C(H)(NO_2)$, $C(H)(CF_3)$, $C(H)(SO_2CH_3)$, or $C(H)(SO_2CF_3)$.

8. A transparent nonlinear optical medium comprising a polymer in accordance with claim 7.

9. A transparent nonlinear optical medium in accordance with claim 8, which is characterized by an external field-induced orientation of aligned m monomer units.

10. An acrylate polymer which is characterized by recurring monomer units corresponding to the formula:

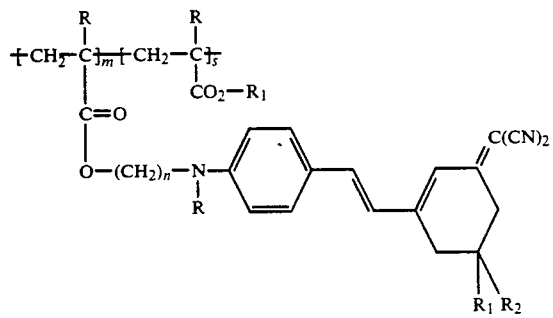

where m and s are integers which total at least 10, and the m monomar comprises between about 10-100 mole percent of the total (m+s) monomer units; n is an integer between; 1 and about 12 ; R is hydrogen or methyl group; and $R_1$ and $R_2$ are a C1-C6 alkyl groups.

11. An acrylate polymer as described in claim 10, where the m monomer comprises about 50 mole percent of the total (m+s) monomer units, $R_1$ and $R_2$ are both methyl groups, and n is 2.

12. A transparent nonlinear optical medium comprising a polymer in accordance with claim 11.

13. A transparent nonlinear optical medium in accordance with claim 12 which is characterized by an external field-induced orientation of aligned m monomer side chains.

14. An optical light switch or modulator device with a polymeric nonlinear optical component comprising a transparent solid medium of an acrylate polymer described in claim 10.

15. An optical light switch or light modulator device with a polymeric nonlinear optical component comprising a transparent solid medium of a vinyl polymer which is characterized by recurring monomeric units corresponding to the formula:

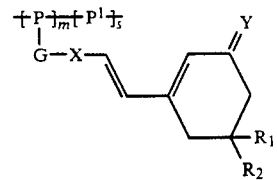

where P and $P^1$ represent vinyl monomer moieties forming the polymer backbone, m and s are integers which total at least 10, and the m monomer comprises between about 10-100 mole percent of the total (m+s) monomer units; G represents a spacer group, $R_1$ and $R_2$ may be the same or different and are selected from the group consisting of hydrogen, C1-C6 alkyls and C1-C6 haloalkyls; X represents an electron donor group capable of donating electrons to the pi-system, and Y represents an electron acceptor group.

16. An optical device in accordance with claim 15, wherein said polymeric nonlinear optical component exhibits less than about 15 percent scattering of transmitted incident light.

17. An optical light switch or light modulator device with a polymeric nonlinear optical component comprising a transparent solid medium of a vinyl polymer corresponding to the formula:

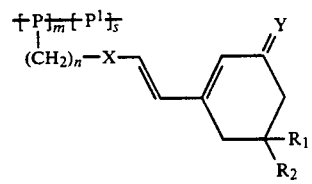

where P and $P^1$ represent vinyl monomer moieties forming the polymer backbone, m and s are integers which total at least 10, and the m monomer comprises between about 10-100 mole percent of the total (m+s) monomer units; n is an integer between 1 and about 12; $R_1$ and $R_2$ may be the same or different and are selected from the group consisting of hydrogen, C1-C6 alkyls and C1-C6 haloalkyls; X is

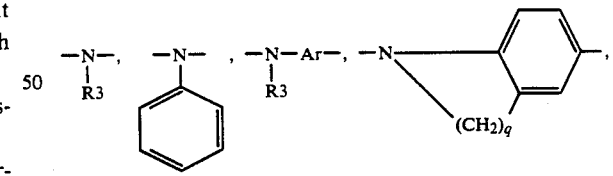

—O—, or —S—, R3 is hydrogen or a C1-C4 alkyl, q is 2-3, and Ar is 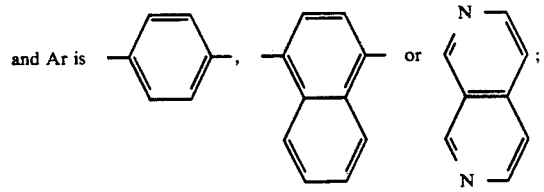

and Y is $(C(CN)_2$, $C(H)(CH)$, $C(H)(NO_2)$, $C(H)(CF_3)$, $C(H)(SO_2CH_3)$, or $C(H)(SO_2CF_3)$.

18. A copolymer which is characterized by recurring monomeric units corresponding to the formula:

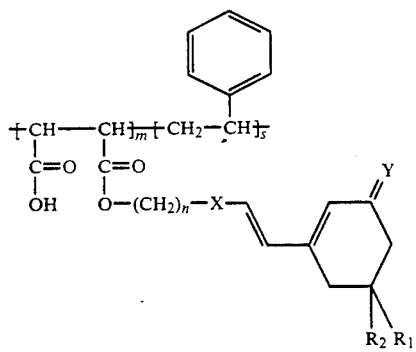

where m and s are integers which total at least 10, and the m monomer comprises about 10-50 mole percent of the total (m+s) monomer units; n is an integer with a value of 1-12; $R_1$ and $R_2$ may be the same or different and are selected from the group consisting of hydrogen, $C_1$-$C_6$ alkyls and $C_1$-$C_6$ haloalkyls; X is

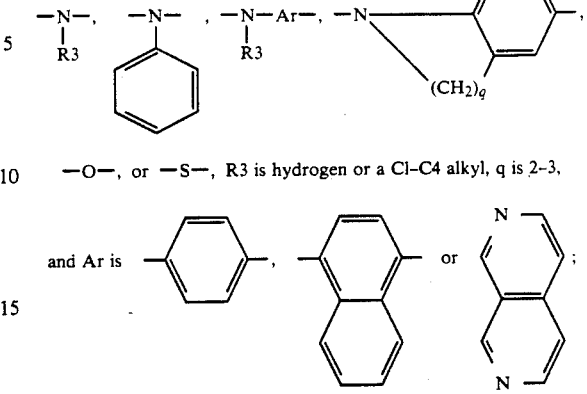

—O—, or —S—, R3 is hydrogen or a Cl-C4 alkyl, q is 2-3, and Y is $C(CN)_2$, $C(H)(CN)$, $C(H)(NO_2)$, $C(H)(CF_3)$, $C(H)(SO_2CH_3)$, or $C(H)(SO_2CF_3)$.

* * * * *